(12) United States Patent
Lee et al.

(10) Patent No.: US 7,442,793 B2
(45) Date of Patent: Oct. 28, 2008

(54) PEPTIDE DEFORMYLASE INHIBITORS

(75) Inventors: Jinhwa Lee, Collegeville, PA (US); Siegfried B. Christensen, IV, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 472 days.

(21) Appl. No.: 10/538,625

(22) PCT Filed: Dec. 11, 2003

(86) PCT No.: PCT/US03/39528

§ 371 (c)(1),
(2), (4) Date: Jun. 10, 2005

(87) PCT Pub. No.: WO2004/052919

PCT Pub. Date: Jun. 24, 2004

(65) Prior Publication Data

US 2007/0173542 A1    Jul. 26, 2007

(51) Int. Cl.
 C07D 237/26 (2006.01)
 C07D 215/38 (2006.01)
 C07D 407/00 (2006.01)
 C07D 319/14 (2006.01)

(52) U.S. Cl. .......... 544/235; 546/153; 546/156; 546/161; 549/414; 549/425; 549/377; 549/366; 549/439; 549/58; 549/59; 549/72; 549/468; 549/487

(58) Field of Classification Search ......... 546/153, 546/161, 156; 544/235; 549/487, 468, 59, 549/72, 58, 377, 366, 439, 414, 425
See application file for complete search history.

(56) References Cited

FOREIGN PATENT DOCUMENTS

| JP | 11080131 | 3/1999 |
| WO | WO 99/39704 | 8/1999 |
| WO | WO99/39704 | * 8/1999 |
| WO | WO 00/35440 | 6/2000 |
| WO | WO 00/58294 | 10/2000 |

* cited by examiner

Primary Examiner—D. Margaret Seaman
(74) Attorney, Agent, or Firm—Laura K. Madden; Loretta Sauermelch; Mary McCarthy

(57) ABSTRACT

Novel PDF inhibitors and novel methods for their use are provided.

5 Claims, No Drawings

PEPTIDE DEFORMYLASE INHIBITORS

This application is a 371 of International Application No. PCT/US2003/039528, filed 11 Dec. 2003.

FIELD OF THE INVENTION

The present invention relates to the use of novel antibacterial compounds, and pharmaceutical compositions containing these compounds as peptide deformylase inhibitors.

BACKGROUND OF THE INVENTION

Bacterial initiator methionyl tRNA is modified by methionyl tRNA formyltransferase (FMT) to produce formyl-methionyl tRNA. The formyl methionine (f-met) is then incorporated at the N-termini of newly synthesized polypeptides. Polypeptide deformylase (PDF or Def) then deformylates primary translation products to produce N-methionyl polypeptides. Most intracellular proteins are further processed by methionine amino peptidase (MAP) to yield the mature peptide and free methionine, which is recycled. PDF and MAP are both essential for bacterial growth, and PDF is required for MAP activity. This series of reactions is referred to as the methionine cycle.

To date, polypeptide deformylase homologous genes have been found in bacteria, in chloroplast-containing plants, in mice and in human. The plant proteins are nuclear encoded but appear to carry a chloroplast localisation signal. This is consistent with the observation that chloroplast RNA and protein synthesis processes are highly similar to those of eubacteria. While there is limited information on protein expression of mammalian PDF gene homologs (Bayer Aktiengesellschaft, Pat. WO2001/42431), no functional role for such proteins has been demonstrated to date (Meinnel, T., Parasitology Today 16(4), 165-168, 2000).

Polypeptide deformylase is found in all eubacteria for which high coverage genomic sequence information is available. Sequence diversity among PDF homologs is high, with as little as 20% identity between distantly related sequences. However, conservation around the active site is very high, with several completely conserved residues, including one cysteine and two histidines which are required to coordinate the active site metal (Meinnel, T. et al., J. Mol. Biol. 267, 749-761, 1997).

PDF is recognized to be an attractive antibacterial target, as this enzyme has been demonstrated to be essential for bacterial growth in vitro (Mazel, D. et al., EMBO J. 13 (4), 914-923, 1994), is not believed to be involved in eukaryotic protein synthesis (Rajagopalan et al., J. Am. Chem. Soc. 119, 12418-12419, 1997), and is universally conserved in prokaryotes (Kozak, M., Microbiol. Rev. 47, 1-45, 1983). Therefore PDF inhibitors can potentially serve as broad spectrum antibacterial agents.

SUMMARY OF THE INVENTION

The present invention involves novel antibacterial compounds represented by Formula (1) hereinbelow and their use as PDF inhibitors.

DETAILED DESCRIPTION OF THE INVENTION

In one aspect of the present invention, there is provided a compound of formula (1):

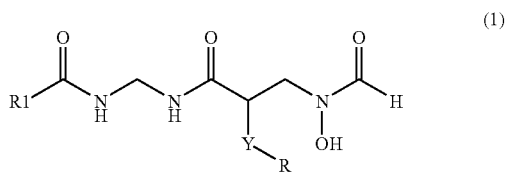

wherein:
R is selected from the group consisting of:
  $C_{2-6}$ alkyl (optionally substituted by alkoxy, halogen, or $C_{1-3}$ alkylsulfanyl);
  $C_{2-6}$ alkenyl (optionally substituted by alkoxy, halogen, or $C_{1-3}$ alkylsulfanyl);
  $C_{2-6}$ alkynyl (optionally substituted by alkoxy, halogen, or $C_{1-3}$ alkylsulfanyl);
  $(CH_2)_n$—$C_{3-6}$ carbocycle (optionally substituted by alkoxy, halogen, or $C_{1-3}$ alkylsulfanyl); and $(CH_2)_n$—R2, wherein R2 is selected from the group consisting of phenyl, furan, benzofuran, thiophene, benzothiophene, tetrahydrofuran, tetrahydropyran, dioxane, 1,4-benzodioxane or benzo[1,3]dioxole; R2 is optionally substituted by one or more substituent selected from Cl, Br, I, $C_{1-3}$ alkyl (optionally substituted by one to three F) and $C_{1-2}$ alkoxy (optionally substituted by one to three F);
R1 is selected from the group consisting of aryl and heteroaryl;
Y represents O, $CH_2$ or a covalent bond; and
n is an integer from 0 to 2;
or a salt, solvate, or physiologically functional derivative thereof.

In this invention the most preferred absolute configuration of compounds of the formula (1) is indicated below:

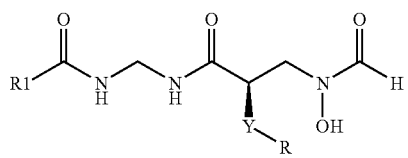

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl, hexyl and the like.

As used herein, the term "substituted alkyl" refers to a straight or branched chain saturated hydrocarbon radical, optionally substituted with substituents selected from the group that includes $C_{1-3}$ alkyl (optionally substituted by one to three fluorines), $C_{2-3}$ alkenyl, $C_{2-3}$ alkynyl, $C_{1-2}$ alkoxy (optionally substituted by one to three fluorines), sulfanyl, sulfinyl, sulfonyl, oxo, hydroxy, mercapto, amino, guanidino, carboxy, aminocarbonyl, aryl, aryloxy, heteroaryl, heteroaryloxy, heterocyclic, aminosulfonyl, sulfonylamino, carboxyamide, ureido, nitro, cyano and halogen, multiple degrees of substitution being allowed.

As used herein, the term "alkenyl" refers to a straight or branched chain hydrocarbon radical having at least one carbon-carbon double bond. Examples of "alkenyl" as used herein include, but are not limited to, ethenyl and propenyl.

As used herein, the term "substituted alkenyl" refers to a straight or branched chain hydrocarbon radical having at least one carbon-carbon double bond, optionally substituted with substituents selected from the group which includes $C_{1-3}$ alkyl (optionally substituted by one to three F), amino, aryl, cyano and halogen, multiple degrees of substitution being allowed.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein, the term "substituted alkynyl" refers to a straight or branched chain hydrocarbon radical having at least one carbon-carbon triple bond, optionally substituted with substituents selected from the group which includes $C_{1-3}$ alkyl (optionally substituted by one to three F), amino, aryl and halogen, multiple degrees of substitution being allowed.

As used herein, the term "halogen" refers to fluorine (F), chlorine (Cl), bromine (Br), or iodine (I), and "halo" refers to the halogen radicals fluoro, chloro, bromo and iodo.

As used herein, the term "carbocycle" refers to a non-aromatic cyclic hydrocarbon radical having from three to seven carbon atoms. For carbocycles with five- to seven-membered rings, a ring double bond is allowed. Exemplary "carbocycle" groups include, but are not limited to, cyclopropyl, cyclobutyl, cyclopentyl, cyclopentenyl, cyclohexyl, and cycloheptyl.

As used herein, the term "substituted carbocycle" refers to a non-aromatic cyclic hydrocarbon radical having from three to seven carbon atoms, and which is optionally substituted with substituents selected from the group which includes $C_{1-3}$ alkyl (optionally substituted by one to three F), $C_{2-3}$ alkenyl, $C_{2-3}$ alkynyl, $C_{1-2}$ alkoxy (optionally substituted by one to three F), sulfanyl, sulfinyl, sulfonyl, oxo, hydroxy, mercapto, amino, guanidino, carboxy, aminocarbonyl, aryl, aryloxy, heteroaryl, heterocyclic, aminosulfonyl, sulfonylamino, carboxyamide, nitro, ureido, cyano and halogen, multiple degrees of substitution being allowed. For carbocycles with five- to seven-membered rings, a ring double bond is allowed.

As used herein, the term "aryl" refers to an optionally substituted benzene ring or to an optionally substituted benzene ring fused to one or more optionally substituted benzene rings to form a ring system. Exemplary optional substituents include $C_{1-3}$ substituted alkyl, $C_{2-3}$ substituted alkenyl, $C_{2-3}$ substituted alkynyl, heteroaryl, heterocyclic, aryl, $C_{1-3}$ alkoxy (optionally substituted by one to three F), aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido, multiple degrees of substitution being allowed. Such a ring or ring system may be optionally fused to one or more optionally substituted aryl rings (including benzene rings), carbocycle rings or heterocyclic rings. Examples of "aryl" groups include, but are not limited to, phenyl, naphthyl, tetrahydronaphthyl, biphenyl, indanyl, anthracyl or phenanthryl, as well as substituted derivatives thereof.

As used herein, the term "heteroaryl" refers to an optionally substituted monocyclic five to six membered aromatic ring containing one or more heteroatomic substitutions selected from S, SO, $SO_2$, O, N, or N-oxide, or to such an aromatic ring fused to one or more optionally substituted rings, such as heteroaryl rings, aryl rings, heterocyclic rings, or carbocycle rings (e.g., a bicyclic or tricyclic ring system). Examples of optional substituents are selected from the group which includes $C_{1-3}$ substituted alkyl, $C_{2-3}$ substituted alkenyl, $C_{2-3}$ substituted alkynyl, heterocyclic, heteroaryl, aryl, $C_{1-3}$ alkoxy (optionally substituted by one to three F), aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen or ureido, multiple degrees of substitution being allowed. Examples of "heteroaryl" groups used herein include, but are not limited to, benzoimidazolyl, benzothiazolyl, benzoisothiazolyl, benzothiophenyl, benzopyrazinyl, benzotriazolyl, benzotriazinyl, benzo[1,4]dioxanyl, benzofuranyl, 9H-α-carbolinyl, cinnolinyl, 2,3-dihydro-[1,4]dioxino[2,3-b]-pyridinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrazolopyridinyl, pyrrolizinyl, pyridazyl, pyrazinyl, pyrimidyl, 4-oxo-1,2-dihydro-4H-pyrrolo[3,2,1-ij]-quinolinyl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted versions thereof.

As used herein, the term "alkoxy" refers to the group —$OR_a$, where $R_a$ is alkyl as defined above. Exemplary alkoxy groups useful in the present invention include, but are not limited to, methoxy, difluoromethoxy, trifluoromethoxy, ethoxy, n-propoxy, isopropoxy, n-butoxy, and t-butoxy.

As used herein the term "aralkoxy" refers to the group —$OR_aR_b$, where $R_a$ is alkyl and $R_b$ is aryl as defined above.

As used herein the term "aryloxy" refers to the group —$OR_a$, where $R_a$ is aryl as defined above.

As used herein, the term "mercapto" refers to the group —SH.

As used herein, the term "sulfanyl" refers to the group —$SR_a$, where $R_a$ is substituted alkyl, substituted carbocycle, aryl, heteroaryl or heterocyclic, as defined above.

As used herein, the term "sulfinyl" refers to the group —$S(O)R_a$, where $R_a$ is substituted alkyl, substituted carbocycle, aryl, heteroaryl or heterocyclic, as defined above.

As used herein, the term "sulfonyl" refers to the group —$S(O)_2R_a$, where $R_a$ is substituted alkyl, substituted carbocycle, aryl, heteroaryl or heterocyclic, as defined above.

As used herein, the term "oxo" refers to the group =O.

As used herein, the term "hydroxy" refers to the group —OH.

As used herein, the term "amino" refers to the group —$NH_2$. The amino group is optionally substituted by substituted alkyl, substituted carbocycle, aryl, heteroaryl or heterocyclic, as defined above.

As used herein, the term "cyano" refers to the group —CN.

As used herein, the term "aminosulfonyl" refers to the group —$S(O)_2NH_2$. The aminosulfonyl group is optionally substituted by substituted alkyl, substituted carbocycle, aryl, heteroaryl or heterocyclic, as defined above.

As used herein, the term "sulfonylamino" refers to the group —$NHS(O)_2R_a$ where $R_a$ is substituted alkyl, substituted carbocycle, aryl, heteroaryl or heterocyclic, as defined above.

As used herein, the term "carboxyamide" refers to the group —$NHC(O)R_a$ where $R_a$ is substituted alkyl, substituted carbocycle, aryl, heteroaryl or heterocyclic, as defined above.

As used herein, the term "carboxy" refers to the group —C(O)OH. The carboxy group is optionally substituted by substituted alkyl, substituted carbocycle, aryl, heteroaryl or heterocyclic, as defined above.

As used herein, the term "aminocarbonyl" refers to the group —$C(O)NH_2$. The aminocarbonyl group is optionally substituted by substituted alkyl, substituted carbocycle, aryl, heteroaryl or heterocyclic, as defined above.

As used herein, the term "ureido" refers to the group —NHC(O)NHR$_a$ wherein R$_a$ is hydrogen, alkyl, carbocycle or aryl as defined above.

As used herein, the term "guanidino" refers to the group —NHC(=NH)NH$_2$.

As used herein, the term "acyl" refers to the group —C(O)R$_a$, where R$_a$ is alkyl, carbocycle, or heterocyclic as defined herein.

As used herein, the term "aroyl" refers to the group —C(O)R$_a$, where R$_a$ is aryl as defined herein.

As used herein, the term "heteroaroyl" refers to the group —C(O)R$_a$, where R$_a$ is heteroaryl as defined herein.

As used herein, the term "acyloxy" refers to the group —OC(O)R$_a$, where R$_a$ is alkyl, carbocycle, or heterocyclic as defined herein.

As used herein, the term "aroyloxy" refers to the group —OC(O)R$_a$, where R$_a$ is aryl as defined herein.

As used herein, the term "heteroaroyloxy" refers to the group —OC(O)R$_a$, where R$_a$ is heteroaryl as defined herein.

Also included in the present invention are pharmaceutically acceptable salts and complexes, such as the hydrochloride, hydrobromide and trifluoroacetate salts and the sodium, potassium and magnesium salts. The compounds of the present invention may contain one or more asymmetric carbon atoms and may exist in racemic and optically active forms. All of these compounds and diastereomers are contemplated to be within the scope of the present invention.

Preferred compounds useful in the present invention are selected from the group consisting of:

Quinoline-8-carboxylic acid ((R)-2-[(formyl-hydroxy-amino)-methyl]-heptanoylamino)-methyl)-amide.
1,2,3,4-Tetrahydro-quinoline-8-carboxylic acid ({(R)-2-[(formyl-hydroxy-amino)-methyl]-heptanoylamino}-methyl)-amide.
Benzofuran-2-carboxylic acid ({(R)-2-[(formyl-hydroxy-amino)-methyl]-heptanoylamino}-methyl)-amide.
Quinoline-6-carboxylic acid ({(R)-2-[(formyl-hydroxy-amino)-methyl]-heptanoylamino}-methyl)-amide.
1,2,3,4-Tetrahydro-quinoline-6-carboxylic acid ({(R)-2-[(formyl-hydroxy-amino)-methyl]-heptanoylamino}-methyl)-amide.
2,3-Dihydro-benzo[1,4]dioxine-6-carboxylic acid ({(R)-2-[(formyl-hydroxy-amino)-methyl]-heptanoyl]amino}-methyl)-amide.
7-Methoxy-benzofuran-2-carboxylic acid ({(R)-2-[(formyl-hydroxy-amino)-methyl]-heptanoylamino}-methyl)-amide.
5-Methoxy-benzofuran-2-carboxylic acid ({(R)-2-[(formyl-hydroxy-amino)-methyl]-heptanoylamino}-methyl)-amide.
3,4-Dihydro-2H-benzo[b][1,4]dioxepine-7-carboxylic acid ({(R)-2-[(formyl-hydroxy-amino)-methyl]-heptanoyl amino}-methyl)-amide.
5-Trifluoromethyl-furan-2-carboxylic acid ({(R)-2-[(formyl-hydroxy-amino)-methyl]-heptanoylamino}-methyl)-amide.
3,4-Difluoro-N-({(R)-2-[(formyl-hydroxy-amino)-methyl]-heptanoylamino}-methyl)-benzamide.
2,3-Difluoro-N-({(R)-2-[(formyl-hydroxy-amino)-methyl]-heptanoylamino}-methyl)-benzamide.
[1,8]Naphthyridine-2-carboxylic acid ({(R)-2-[(formyl-hydroxy-amino)-methyl]-heptanoylamino}-methyl)-amide.
3-Methyl-benzofuran-2-carboxylic acid ({(R)-2-[(formyl-hydroxy-amino)-methyl]-heptanoylamino}-methyl)-amide.
Benzo[1,3]dioxole-5-carboxylic acid ({(R)-2-[(formyl-hydroxy-amino)-methyl]-heptanoylamino}-methyl)-amide.
Benzofuran-2-carboxylic acid {[(R)-2-cyclopentylmethyl-3-(formyl-hydroxy-amino)-propanoylamino]-methyl}-amide.
Benzofuran-2-carboxylic acid ({(R)-7,7,7-trifluoro-2-[(formyl-hydroxy-amino)-methyl]-heptanoylamino}-methyl)-amide.

General Synthetic Sequence

The compounds and processes of the present invention will be better understood in connection with the following synthetic schemes, which are merely illustrative of the methods by which the compounds of the invention may be prepared and are not intended to limit the scope of the invention as defined in the appended claims.

The present invention provides compounds of Formula (1) that can be prepared from the common racemic intermediate (8), or common chiral intermediates (17) and (25).

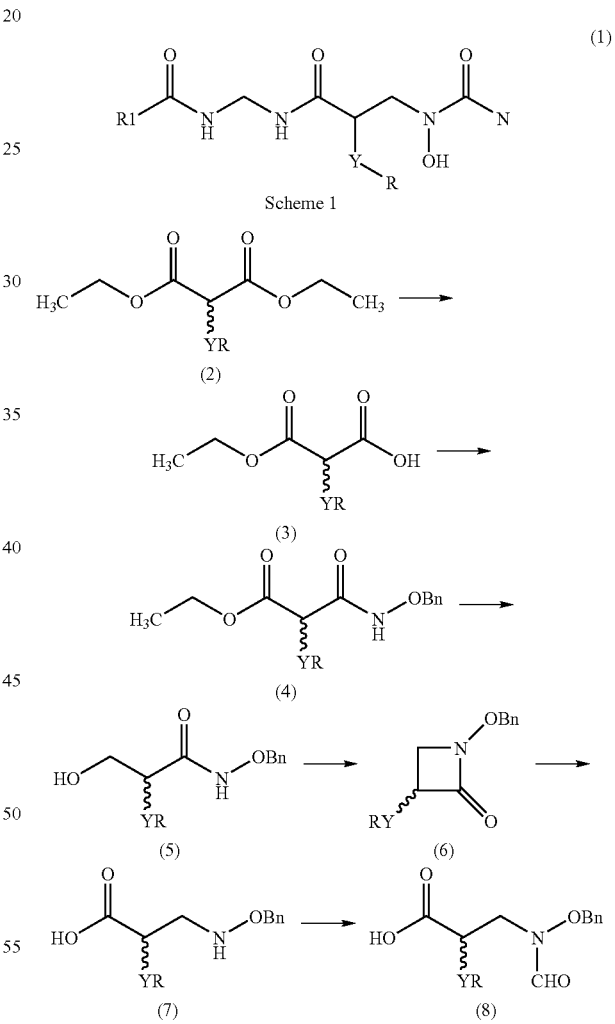

Scheme 1

As shown in Scheme 1, intermediate (8) can be prepared by reacting the mono-substituted dialkyl malonate (2) with a base, such as potassium hydroxide, in an appropriate solvent, such as ethanol/water, to afford the mono-acid (3). Coupling of (3) with O-benzylhydroxylamine in the presence of a coupling reagent, such as 1-[3-(dimethylamino)propyl]-3-ethyl-carbodiimide hydrochloride (EDCI), and a base, such as 4-dimethylaminopyridine (DMAP), in an appropriate solvent, such as dichloromethane, gives the amide (4). Reduction of the ester functionality of compound (4) with a reducing agent, such as lithium borohydride, in an appropriate solvent, such as tetrahydrofuran, at room temperature provides the alcohol (5). Treatment of the alcohol (5) under Mitsunobu conditions affords the lactam (6). The same transformation may be achieved by treating (5) with triphenylphosphine, carbon tetrachloride and a base, such as triethylamine, to obtain (6). Hydrolysis of the lactam (6) using, for example, lithium hydroxide in an appropriate solvent mixture, such as THF-H$_2$O-MeOH, gives acid (7). Formylation of the amine group of (7) is achieved using formic acid and acetic anhydride in a solvent, such as dichloromethane, to provide the formylated compound (8).

Any racemates can be resolved at the level of any intermediate during the synthesis or at the level of the final product using, for example, a chiral chromatography method, to provide compound (8) in each of two enantiomeric forms.

Alternatively, an enantiomer of intermediate (8), such as (17) in Scheme 2 or (25) in Scheme 3, can be prepared by reacting an appropriate acid chloride (9) with a chiral agent, such as Evans' chiral oxazolidinone, in the presence of a base, such as n-butyl lithium, to afford the chiral intermediate (10) in Scheme 2 or (18) in Scheme 3. Treatment of the compound (10) or (18) with a base, such as diisopropylethylamine, in the presence of a chelating agent, such as titanium tetrachloride, in a solvent, such as tetrahydrofuran, followed by addition of an electrophile, such as benzyloxymethylchloride, provides either of two chiral compounds (11) or (19), depending on the selection of chiral auxiliary.

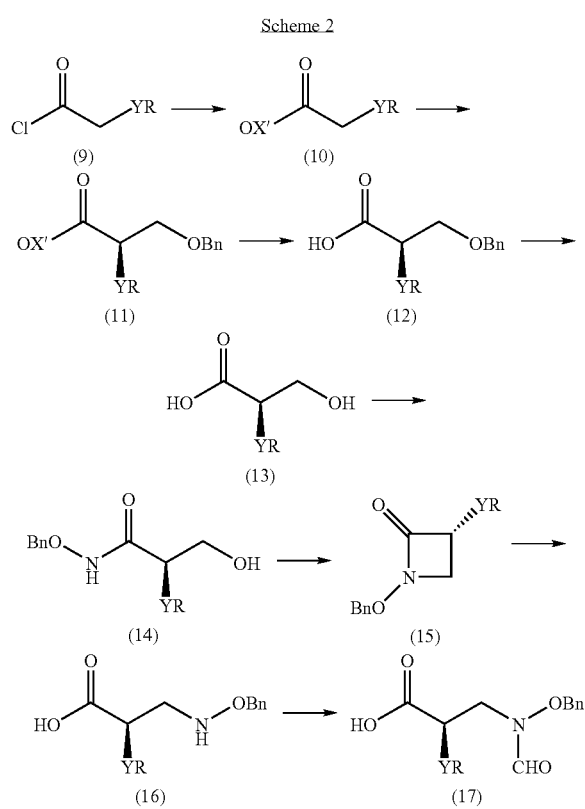

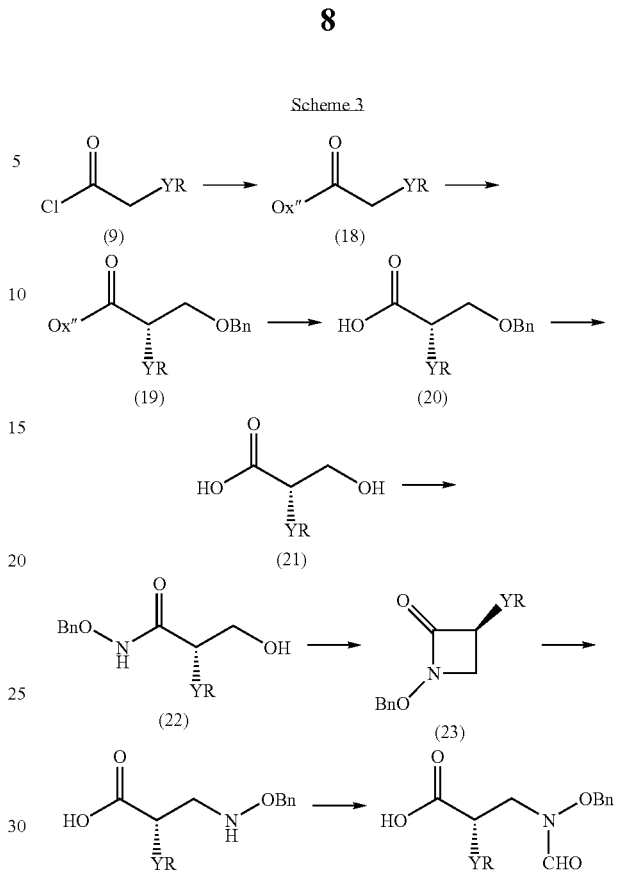

Conversion of compound (11) or (19) to the corresponding hydroxyacid (13) or (21) can be achieved by a sequence comprising oxidative cleavage of the chiral oxazolidinone, using, for example H$_2$O$_2$ and lithium hydroxide, to the respective intermediates (12) or (20), followed by hydrogenolysis. Coupling of the acid (13) or (21) with benzyloxyamine in the presence of coupling agents, such as EDCI/DMAP, yields the amides (14) or (22), respectively. These can be cyclized to the azetidin-2-ones (15) or (23) using Mitsunobu conditions or a combination of triphenylphosphine/carbon tetrachloride/triethylamine. Hydrolysis of the azetidin-2-one (15) or (23), using for example lithium hydroxide, in an appropriate solvent, gives the corresponding acid (16) or (24), respectively. Conversion of compound (16) or (24) to the formate (17) or (25) can be achieved using an appropriate formylating agent, such as formic acid/acetic anhydride or methyl formate, in an appropriate solvent, such as dichloromethane.

As shown in Scheme 4, coupling of carboxylic acid R1COOH (26) with glycinamide hydrochloride, using conditions such as DMAP/EDCI or EDCI/HOAt/NMM, provides the N-carbamoylmethyl amide (27). Rearrangement of (27) using [bis(trifluoroacetoxy)iodo]-benzene (PIFA) in a solvent such as a mixture of acetonitrile and water, followed by treatment with an cid such as hydrochloric acid, affords the N-aminomethyl amide as the corresponding salt (28). Coupling of (28) with acid (8), using conditions such as DMAP/EDCI or EDCI/HOAt/NMM, provides (29), which can be debenzylated by hydrogenation using a catalyst, such as 10% Pd/C, in an appropriate solvent, such as ethanol, to give the desired compound (1). Similarly, coupling of the chiral acid (17) or (25) with (28) provides the corresponding product

(30) or (31). Hydrogenolysis of the benzyl group gives the final desired compound (32) or (33).

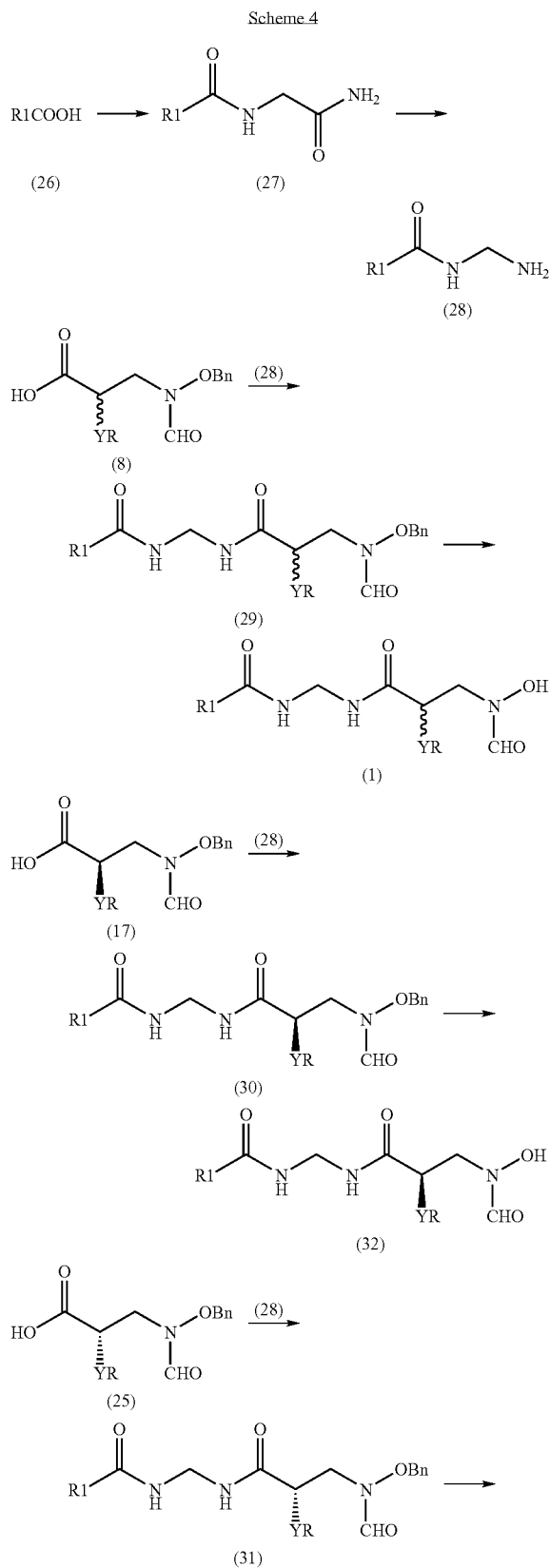

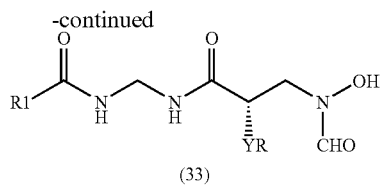

SYNTHETIC EXAMPLES

The invention will now be described by reference to the following examples which are merely illustrative and are not to be construed as a limitation of the scope of the present invention.

As used herein the symbols and conventions used in these processes, schemes and examples are consistent with those used in the contemporary scientific literature, for example, the *Journal of the American Chemical Society or the Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification.

Hz (Hertz); TLC (thin layer chromatography);
Tr (retention time); RP (reverse phase);
MeOH (methanol); i-PrOH (isopropanol);
EtOH (ethanol); TEA (triethylamine);
TFA (trifluoroacetic acid); THF (tetrahydrofuran);
DMSO (dimethylsulfoxide); AcOEt or EtOAc (ethyl acetate);
DCM (dichloromethane); DMF (N,N-dimethylformamide);
CDI (1,1-carbonyldiimidazole); HOAc (acetic acid);
HOSu (N-hydroxysuccinimide); Ac (acetyl);
HOBT (1-hydroxybenzotriazole); BOC (tert-butyloxycarbonyl);
mCPBA (meta-chloroperbenzoic acid); FMOC (9-fluorenylmethoxycarbonyl);
DCC (dicyclohexylcarbodiimide); CBZ (benzyloxycarbonyl);
NMM (N-methyl morpholine); HOAt (1-hydroxy-7-azabenzotriazole);
DMAP (4-dimethylaminopyridine); Bn (benzyl);
TBAF (tetra-n-butylammonium fluoride);
HPLC (high pressure liquid chromatography);
BOP (bis(2-oxo-3-oxazolidinyl)phosphinic chloride);
EDCI (1-ethyl-3-[3-dimethylaminopropyl]carbodiimide hydrochloride);
HBTU (O-Benzotriazole-1-yl-N,N,N',N'-tetramethyluronium hexafluorophosphate);
PIFA ([bis(trifluoroacetoxy)iodo]-benzene).

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted, and all solvents are highest available purity unless otherwise indicated.

$^1$H NMR (hereinafter also "NMR") spectra were recorded on a Varian VXR-300, a Varian Unity-300, a Varian Unity-400 instrument, a Brucker AVANCE-400, a General Electric QE-300 or a Bruker AM 400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Mass spectra were run on an open access LC-MS system using electrospray ionization. LC conditions: 4.5% to 90% $CH_3CN$ (0.02% TFA) in 3.2 min with a 0.4 min hold and 1.4 min re-equilibration; detection by MS, UV at 214 nm, and a light scattering detector (ELS). Column: 1×40 mm Aquasil (C18).

For preparative (prep) hplc; ca 50 mg of the final products were injected in 500 uL of DMSO onto a 50×20 mm I. D. YMC CombiPrep ODS-A column at 20 mL/min with a 10 min gradient from 10% $CH_3CN$ (0.1% TFA) to 90% $CH_3CN$ (0.1% TFA) in $H_2O$ (0.1% TFA) and a 2 min hold. Flash chromatography was run over Merck Silica gel 60 (230-400 mesh).

Infrared (IR) spectra were obtained on a Nicolet 510 FT-IR spectrometer using a 1-mm NaCl cell. Most of the reactions were monitored by thin-layer chromatography on 0.25 mm E. Merck silica gel plates (60 F-254), visualized with UV light, 5% ethanolic phosphomolybdic acid or p-anisaldehyde solution.

The following synthetic schemes are merely illustrative of the methods by which the compounds of the invention may be prepared and are not intended to limit the scope of the invention as defined in the appended claims.

The compounds disclosed in Examples 2 to 32 were prepared following the general procedures described in Example 1. The compounds disclosed in Examples 34 to 47 were prepared following the general procedures described in Example 33.

Preparation 1

(4S)-Benzyl-3-heptanoyl-oxazolidin-2-one

To a solution of (S)-(−)-4-benzyl-2-oxazolidinone (3.3 g, 18.6 mmol) in THF (50 mL) at −78° C. was added dropwise n-BuLi (7.4 mL, 2.5M solution in hexane, 18.6 mmol). After stirring for 30 min at the same temperature, the reaction mixture was then treated with heptanoyl chloride (2.76 g, 18.6 mmol). The reaction mixture was stirred and allowed to warm to 10° C. over 5 h, and then quenched with saturated aqueous $NH_4Cl$ solution (100 mL). The aqueous layer was extracted with EtOAc (100 mL×2). The combined organic layers were washed with brine, and dried over $MgSO_4$. Removal of the solvent under reduced pressure yielded the title compound. $^1H$ NMR (400 MHz, $CDCl_3$) δ 7.37-7.22 (m, 5H), 4.69 (m, 1H), 4.19 (m, 2H), 3.31 (dd, J=13.4, 3.3 Hz, 1H), 2.95 (m, 2H), 2.79 (dd, J=13.4, 9.7 Hz, 1H), 1.71 (m, 2H), 1.42-1.32 (m, 6H), 0.92 (t, J=6.8 Hz, 3H). MH+290.

Preparation 2

(4S)-Benzyl-3-[(2R)-benzyloxymethylheptanoyl] oxazolidin-2-one

To a solution of (S)-4-benzyl-3-heptanoyloxazolidin-2-one (4.63 g, 16.02 mmol) and titanium (IV) chloride (1.9 mL, 16.82 mmol) in dichloromethane (55 mL) at 0° C. was added dropwise diisopropylethylamine (3.1 mL, 17.62 mmol). After stirring at 0° C. for 1 hour, the resulting titanium enolate was then reacted with benzylchloromethyl ether (TCI-America, 4.9 mL, 32.04 mmol) at 0° C. for 6 h. The reaction mixture was then quenched with water (100 mL). The aqueous layer was extracted with dichloromethane (100 mL×2). The organic extracts were washed with brine, and dried over $MgSO_4$. After removing the solvent under reduced pressure, purification by flash column chromatography using an eluting system of hexane/EtOAc (5:1) yielded the title compound. $^1H$ NMR (400 MHz, $CDCl_3$) δ 7.38-7.21 (m, 10H), 4.74 (m, 1H), 4.57 (m, 2H), 4.28-4.13 (m, 3H), 3.82 (t, J=8.7 Hz, 1H), 3.68 (dd, J=9.0, 4.9 Hz, 1H), 3.25 (dd, J=13.5, 3.1 Hz, 1H), 2.71 (dd, J=13.5, 9.3 Hz, 1H), 1.74 (m, 1H), 1.54 (m, 1H), 1.31-1.28 (m, 6H), 0.89 (t, J=6.7 Hz, 3H). MH+410.

Preparation 3

(3R)-Benzyloxy-2-pentylpropionic acid

A 0.05 M solution of (S)-4-benzyl-3-[(R)-2-benzyloxymethylheptanoyl]oxazolidin-2-one (2.0 g, 4.89 mmol) in a 3:1 mixture of THF and $H_2O$ was treated with 30% $H_2O_2$ (4.5 L, 39.12 mmol), followed by LiOH (0.48 g, 9.78 mmol) at 0° C. The resulting mixture was stirred and allowed to warm to room temperature overnight. THF was then removed under vacuum. The residue was washed with dichloromethane (50 mL×2) to remove (S)-4-benzyloxazolidin-2-one. The desired product was isolated by EtOAc extraction of the acidified (pH 1~2) aqueous phase. No further purification was required. Standing under high vacuum yielded the title compound. $^1H$ NMR (400 MHz, $CHCl_3$) δ 11.1 (br s, 1H), 7.36 (m, 5H), 4.57 (s, 2H), 3.69 (m, 1H), 3.58 (dd, J=9.2, 5.2 Hz, 1H), 2.74 (m, 1H), 1.66 (m, 1H), 1.54 (m, 1H), 1.34-1.30 (m, 6H), 0.90 (t, J=6.7 Hz, 3H). MH+251.

Preparation 4

3-Hydroxy-(2R)-pentylpropionic acid

To a solution of (R)-3-benzyloxy-2-pentyl-propionic acid (1.54 g, 6.16 mmol) in EtOH (100 mL) was added 10% Pd/C (310 mg). The reaction mixture was subjected to hydrogenation overnight at room temperature. After the reaction was completed, the reaction mixture was filtered through a pad of Celite, and washed with EtOH (50 mL×3). Removal of the solvent provided the title compound. No further purification was required. $^1H$ NMR (400 MHz, $CHCl_3$) δ 6.30 (br s, 1H), 3.81 (d, J=5.4 Hz, 2H), 2.64 (m, 1H), 1.69 (m, 1H), 1.56 (m, 1H), 1.41-1.27 (m, 6H), 0.91 (t, J=7.7 Hz, 3H). MH+161.

Preparation 5

N-Benzyloxy-3-hydroxy-(2R)-pentylpropionamide

To a mixture of (R)-3-hydroxy-2-pentylpropionic acid (0.92 g, 5.75 mmol), O-benzyl hydroxylamine hydrochloride (0.92 g, 5.75 mmol) and 4-(dimethylamino)pyridine (1.41 g, 11.50 mmol) in dichloromethane (25 mL) at 0° C. was added 1-[3-(dimethylamino)propyl]-3-ethylcarbodiimide hydrochloride (1.11 g, 5.75 mmol). After stirring at room temperature overnight, the reaction was then quenched with 1N aqueous HCl solution (25 mL) and extracted using dichloromethane (25 mL×2). The organic extracts were washed with water, brine, and dried over $MgSO_4$. Removal of the solvent under reduced pressure yielded the title compound. $^1H$ NMR (400 MHz, $CHCl_3$) δ 9.22 (br s, 1H), 7.41-7.28 (m, 5H), 4.89 (q, J=10.6 Hz, 2H), 3.70-3.37 (m, 3H), 2.17 (m, 1H), 1.54 (br s, 1H), 1.27 (m, 6H), 0.88 (t, J=6.9 Hz, 3H). MH+266.

Preparation 6

1-benzyloxy-(3R)-pentyl-azetidin-2-one

To a mixture of (R)—N-benzyloxy-3-hydroxy-2-pentyl-propionamide (1.41 g, 5.32 mmol) and triphenylphosphine (1.68 g, 6.39 mmol) in THF (53 mL) was added dropwise diethyl azodicarboxylate (1.1 mL, 6.39 mmol) at 0° C. The reaction mixture was stirred and allowed to warm to room temperature overnight. The reaction was then quenched with water (50 mL). The aqueous layer was extracted with EtOAc (50 mL×2). The combined organic layers were washed with brine, and dried over $MgSO_4$. After removing the solvent under vacuum, the residue was purified by flash column chromatography (hex:EtOAc 5/1) to provide the title compound. $^1H$ NMR (400 MHz, $CHCl_3$) δ 7.35-7.25 (m, 5H), 4.87 (s, 2H), 3.28 (t, J=4.85 Hx, 1H), 2.84 (q, J=2.35 Hz, 1H), 2.77 (m, 1H), 1.62 (m, 1H), 1.36 (m, 1H), 1.25-1.16 (m, 6H), 0.88 (t, J=6.9 Hz, 3H). MH+248.

Preparation 7

3-benzyloxyamino-(2R)-pentylpropionic acid

To a mixture of (R)-1-benzyloxy-3-pentylazetidin-2-one (0.96 g, 3.89 mmol) in a mixture of $THF-H_2O-MeOH$ (50 mL, 3:1:1 v/v) was added lithium hydroxide monohydrate (1.91 g, 38.9 mmol). After stirring at room temperature overnight, water (25 mL) was added to the mixture. The solution was acidified to pH 5~6 with 3N aqueous HCl solution. It was extracted with EtOAc (50 mL×2). The combined organic layers were dried over $MgSO_4$. Removal of the solvent under vacuum provided the title compound. $^1H$ NMR (400 MHz, $CHCl_3$) δ 9.80 (br s, 1H), 7.37 (m, 5H), 4.75 (m, 2H), 3.14 (m, 2H), 2.74 (m, 1H), 1.70 (m, 1H), 1.53 (m, 1H), 1.38-1.25 (m, 6H), 0.91 (t, J=6.8 Hz, 3H). MH+266.

Preparation 8

(2R)-[(benzyloxyformylamino)methyl]heptanoic acid

To a cold solution of (R)-3-Benzyloxyamino-2-pentylpropionic acid (1.03 g, 3.89 mmol) in $HCO_2H$ (19 mL) and dichloromethane (19 mL) at 0° C. was added acetic anhydride (3.9 mL, 41.2 mmol). The mixture was stirred at 0° C. for 3 hours. The volatiles were removed by evaporation under vacuum. Dichloromethane (50 mL) was added to it. It was washed with brine (50 mL×2), and dried over $MgSO_4$. Filtration and evaporation under vacuum provided the title compound. $^1H$ NMR (400 MHz, $CHCl_3$) δ 8.07 (br s, 1H), 7.29 (m, 5H), 4.91-4.71 (m, 2H), 3.76 (m, 2H), 2.67 (m, 1H), 1.54 (m, 1H), 1.41(m, 1H), 1.20 (m, 6H), 0.80 (t, J=7.0 Hz, 3H). MH+294.

Preparation 9

N-Carbamoylmethyl-quinoline-8-carboxamide

To a mixture of quinoline-8-carboxylic acid (3.45 mmol), glycinamide hydrochloride (3.45 mmol), NMM (41.43 mmol) and HOAt (4.14 mmol) in DMF (17 mL) at room temperature was added 1-[3-(dimethylamino)propyl]-3-ethylcarbodiimide hydrochloride (4.14 mmol). After stirring at room temperature overnight, the reaction mixture was purified by HPLC to afford the title compound as a white solid. MH+230.

Preparation 10

N-Aminomethyl-quinoline-8-carboxamide hydrochloride

PIFA (0.60 mmol) was dissolved in acetonitrile (1.5 mL). To this solution deionized water (1.5 mL) was added. Finally N-carbamoylmethyl-quinoline-8-carboxamide (0.60 mmol) was added, and the reaction mixture was allowed to stir at room temperature overnight. The reaction mixture was diluted with 1N HCl (15 mL) and was washed twice with ether (20 mL×2). The aqueous layer was concentrated under reduced pressure. The resulting residue (white solid) was directly used in the next step.

Preparation 11

Quinoline-8-carboxylic acid ((R)-2-[(formyl-benzyloxy-amino)-methyl]-heptanoylamino}-methyl)-amide To a mixture of (R)-2-[(benzyloxyformyl-amino)methyl] heptanoic acid (0.535 mmol), N-aminomethyl-quinoline-8-carboxamide hydrochloride (0.535 mmol), NMM (5.35 mmol) and HOAt (0.642 mmol) in DMF (6 mL) at room temperature was added 1-[3-(dimethylamino)-propyl]-3-ethylcarbodiimide hydrochloride (0.642 mmol). After stirring at room temperature overnight, the reaction mixture was then purified by HPLC to afford the title compound as a white solid. MH+477.

Example 1

Quinoline-8-carboxylic acid ((R)-2-[(formyl-hydroxy-amino)-methyl]-heptanoylamino}-methyl)-amide To a solution of quinoline-8-carboxylic acid ((R)-2-[(formyl-benzyloxy-amino)-methyl]-heptanoylamino}-methyl)-amide (0.260 mmol) in EtOH (10 mL) was added 10% Pd/C (22 mg). The reaction mixture was subjected to hydrogenation overnight at room temperature. The reaction mixture was then filtered through a pad of Celite, and washed with EtOH (10 mL×2). Removal of the solvent provided the crude product, which was further purified by HPLC to yield the title compound. $^1H$ NMR (400 MHz, $CD_3OD$) δ 9.03 (d, 1H, J=4.2 Hz), 8.70 (d, 1H, J=7.3 Hz), 8.48 (d, 1H, J=8.2 Hz), 8.16 (d, 1H, J=8.2 Hz), 7.88 (s, 1H), 7.74 (t, 1H, J=7.7 Hz), 7.64 (dd, 1H, J=8.2, 4.2 Hz), 4.99 (ab quart, 2H), 3.80-3.33 (m, 2H), 2.85 (m, 1H), 1.55 (m, 1H), 1.45 (m, 1H), 1.30-1.10 (m, 6H), 0.64 (t, 3H, J=7.2 Hz). MH+387.

Example 2

1,2,3,4-Tetrahydro-quinoline-8-carboxylic acid ({(R)-2-[(formyl-hydroxy-amino)-methyl]-heptanoylamino}-methyl)-amide Purification by preparative HPLC yielded the title compound. $^1H$ NMR (400 MHz, $CD_3OD$) δ 7.89 (s, 1H), 7.26 (d, 1H, J=8.0 Hz), 6.98 (d, 1H, J=7.1 Hz), 6.44 (t, 1H, J=7.44 Hz), 4.70 (ab quart, 2H), 3.80-3.35 (m, 2H), 3.35 (m, 2H), 2.82 (m, 1H), 2.77 (t, 2H, J=6.33 Hz), 1.88 (m, 2H), 1.60-1.21 (m, 8H), 0.85 (t, 3H). MH+391.

Example 3

Benzofuran-2-carboxylic acid ({(R)-2-[(formyl-hydroxy-amino)-methyl]-heptanoylamino}-methyl)-amide Purification by preparative HPLC yielded the title compound. $^1$H NMR (400 MHz, CD$_3$OD) δ 7.89 (s, 1H), 7.74 (d, 1H, J=7.8 Hz), 7.60 (d, 1H, J=8.4 Hz), 7.54 (s, 1H), 7.48 (t, 1H), 7.34 (t, 1H), 4.79 (ab quart, 2H), 3.89-3.40 (m, 2H), 2.86 (m, 1H), 1.50 (m, 1H), 1.35 (m, 1H), 1.30 (m, 6H), 0.78 (t, 3H). MH+376.

Example 4

Quinoline-6-carboxylic acid ({(R)-2-[(formyl-hydroxy-amino)-methyl]-heptanoylamino}-methyl)-amide $^1$H NMR (400 MHz, CD$_3$OD) δ 8.95 (d, 1H, J=2.9 Hz), 8.50 (m, 1H), 8.19 (dd, 1H, J=8.9, 2.0 Hz), 8.11 (d, 1H, J=8.9 Hz), 7.91 (s, 1H), 7.64 (dd, 1H, J=8.3, 4.2 Hz), 4.83 (ab quart, 2H), 3.87-3.30 (m, 2H), 2.89 (m, 1H), 1.57 (m, 1H), 1.45 (m, 1H), 1.31-1.23 (m, 6H), 0.80 (t, 3H, J=6.8 Hz). MH+387.

Example 5

1,2,3,4-Tetrahydro-quinoline-6-carboxylic acid ({(R)-2-[(formyl-hydroxy-amino)-methyl]-heptanoylamino}-methyl)-amide

MH+391

Example 6

2,3-Dihydro-benzo[1,4]dioxine-6-carboxylic acid ({(R)-2-[(formyl-hydroxy-amino)-methyl]-heptanoyl]amino}-methyl)-amide $^1$H NMR (400 MHz, CD$_3$OD) δ 7.88 (s, 1H), 7.36 (m, 2H), 6.89 (d, 1H, J=8.4 Hz), 4.73 (ab quart, 2H, J=10.8, 3.7 Hz), 4.28 (m, 4H), 3.80-3.41 (m, 2H), 2.82 (m, 1H), 1.54 (m, 1H), 1.44 (m, 1H), 1.24 (m, 6H), 0.85 (br t, 3H). MH+394.

Example 7

7-Methoxy-benzofuran-2-carboxylic acid ({(R)-2-[(formyl-hydroxy-amino)-methyl]-heptanoylamino}-methyl)-amide $^1$H NMR (400 MHz, CD$_3$OD) δ 7.89 (s, 1H), 7.51 (s, 1H), 7.27 (m, 2H), 7.03 (d, 1H, J=7.5 Hz), 4.78 (ab quart, 2H), 4.01 (s, 3H), 3.75 (m, 2H), 2.85 (m, 1H), 1.55 (m, 1H), 1.44 (m, 1H), 1.27 (m, 6H), 0.77 (t, 3H, J=6.2 Hz). MH+406.

Example 8

5-Methoxy-benzofuran-2-carboxylic acid ({(R)-2-[(formyl-hydroxy-amino)-methyl]-heptanoylamino}-methyl)-amide $^1$H NMR (400 MHz, CD$_3$OD) δ 7.89 (s, 1H), 7.49 (d, 1H, J=2.2 Hz), 7.48 (s, 1H), 7.22 (d, 1H, J=2.5 Hz), 7.07 (dd, 1H, J=9.2, 2.6 Hz), 4.81 (ab quart, 2H), 3.85 (s, 3H), 3.71 (m, 2H), 2.84 (m, 1H), 1.55 (m, 1H), 1.44 (m, 1H), 1.28 (m, 6H), 0.79 (t, 3H, J=7.0 Hz). MH+406.

Example 9

3,4-Dihydro-2H-benzo[b][1,4]dioxepine-7-carboxylic acid ({(R)-2-[(formyl-hydroxy-amino)-methyl]-heptanoylamino}-methyl)-amide $^1$H NMR (400 MHz, CD$_3$OD) δ 7.88 (s, 1H), 7.46 (s, 1H), 7.43 (d, 1H, J=8.3 Hz), 7.00 (d, 1H, J=8.3 Hz), 4.73 (ab quart, 2H), 4.24 (m, 4H), 3.75 (m, 2H), 2.83 (m, 1H), 2.21 (t, 2H), 1.55 (m, 1H), 1.45 (m, 1H), 1.27 (m, 6H), 0.84 (br t, 3H). MH+408.

Example 10

5-Trifluoromethyl-furan-2-carboxylic acid ({(R)-2-[(formyl-hydroxy-amino)-methyl]-heptanoylamino}-methyl)-amide $^1$H NMR (400 MHz, CD$_3$OD) δ 7.87 (s, 1H), 7.26 (d, 1H, J=3.8 Hz), 7.16 (d, 1H, J=3.8 Hz), 4.75 (m, 2H), 3.76 (m, 2H), 2.84 (m, 1H), 1.55 (m, 1H), 1.44 (m, 1H), 1.27 (m, 6H), 0.84 (t, 3H, J=6.5 Hz). MH+394.

Example 11

3,4-Difluoro-N-({(R)-2-[(formyl-hydroxy-amino)-methyl]-heptanoylamino}-methyl)-benzamide $^1$H NMR (400 MHz, CD$_3$OD) δ 7.87 (s, 1H), 7.81 (m, 1H), 7.79 (m, 1H), 7.41 (m, 1H), 4.74 (ab quart, 2H), 3.77 (m, 2H), 2.85 (m, 1H), 1.55 (m, 1H), 1.44 (m, 1H), 1.28 (m, 6H), 0.84 (t, 3H, J=6.8 Hz). MH+372.

Example 12

2,3-Difluoro-N-({(R)-2-[(formyl-hydroxy-amino)-methyl]-heptanoylamino}-methyl)-benzamide $^1$H NMR (400 MHz, CD$_3$OD) δ 7.88 (s, 1H), 7.48 (m, 2H), 7.27 (m, 1H), 4.75 (ab quart, 2H), 3.75 (m, 2H), 2.86 (m, 1H), 1.55 (m, 1H), 1.44 (m, 1H), 1.26 (m, 6H), 0.87 (t, 3H, J=6.5 Hz). MH+372.

Example 13

[1,8]Naphthyridine-2-carboxylic acid ({(R)-2-[(formyl-hydroxy-amino)-methyl]-heptanoylamino}-methyl)-amide $^1$H NMR (400 MHz, CD$_3$OD) δ 9.18 (br s, 1H), 8.64 (d, 1H, J=8.3 Hz), 8.57 (d, 1H, J=8.0 Hz), 8.37 (d, 1H, J=8.3 Hz), 7.77 (m, 1H), 4.85 (ab quart, 2H), 3.76 (m, 2H), 2.84 (m, 1H), 1.55 (m, 1H), 1.45 (m, 1H), 1.25 (m, 6H), 0.73 (t, 3H, J=6.9 Hz). MH+388.

Example 14

3-Methyl-benzofuran-2-carboxylic acid ({(R)-2-[(formyl-hydroxy-amino)-methyl]-heptanoylamino}-methyl)-amide $^1$H NMR (400 MHz, CD$_3$OD) δ 7.89 (s, 1H), 7.67 (t, 1H, J=7.5 Hz), 7.52 (d, 1H, J=7.8 Hz), 7.46 (br s, 1H, J=7.2 Hz), 7.32 (br s, 1H, J=7.2 Hz), 4.78 (ab quart, 2H), 3.70 (m, 2H), 2.85 (m, 1H), 2.59 (s, 3H), 1.55 (m, 1H), 1.46 (m, 1H), 1.26 (m, 6H), 0.76 (br t, 3H). MH+390.

Example 15

Benzo[1,3]dioxole-5-carboxylic acid ({(R)-2-[(formyl-hydroxy-amino)-methyl]-heptanoylamino}-methyl)-amide $^1$H NMR (400 MHz, CD$_3$OD) δ 7.88 (s, 1H), 7.44 (d, 1H, J=8.2 Hz), 7.32 (s, 1H), 6.89 (d, 1H, J=8.2 Hz), 6.05 (s, 2H), 4.73 (ab quart, 2H), 3.76 (m, 2H), 2.85 (m, 1H), 1.55 (m, 1H), 1.46 (m, 1H), 1.27 (m, 6H), 0.86 (t, 3H, J=6.4 Hz). MH+380.

Example 16

Benzofuran-2-carboxylic acid {[(R)-2-cyclopentylmethyl-3-(formyl-hydroxy-amino)-propanoylamino]-methyl}-amide $^1$H NMR (400 MHz, CD$_3$OD) δ 7.88 (s, 1H), 7.74 (d, 1H, J=7.8 Hz), 7.60 (d, 1H, J=8.4 Hz), 7.54 (s, 1H), 7.48 (t, 1H, J=7.5 Hz), 7.34 (t, 1H, J=7.5 Hz), 4.79 (ab quart, 2H), 3.89 (m, 2H), 2.86 (m, 1H), 1.85-1.37 (m, 111H), 0.78 (m, 3H). MH+388.

Example 17

Benzofuran-2-carboxylic acid ({(R)-7,7,7-trifluoro-2-[(formyl-hydroxy-amino)-methyl]-heptanoylamino}-methyl)-amide $^1$H NMR (400 MHz, CD$_3$OD) δ 7.88 (s, 1H), 7.74 (d, 1H, J=7.8 Hz), 7.60 (d, 1H, J=8.4 Hz), 7.54 (s, 1H), 7.48 (t, 1H, J=7.5 Hz), 7.34 (t, 1H, J=7.5 Hz), 4.79 (ab quart, 2H), 3.88 (m, 2H), 2.78 (m, 1H), 1.95 (m, 2H), 1.50-1.21 (m, 6H). MH+430.

Compositions, Administration and Biological Assays

Compounds of Formula (1) and their pharmaceutically acceptable salts may be administered in a standard manner for antibiotics, for example orally, parenterally, sublingually, dermally, transdermally, rectally, via inhalation or via buccal administration.

Compositions of Formula (1) and their pharmaceutically acceptable salts which are active when given orally can be formulated as syrups, tablets, capsules, creams and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions or suspensions may be considered, for example, aqueous gums, celluloses, silicates or oils, and incorporated in a soft gelatin capsule shell.

Typical parenteral compositions consist of a solution or suspension of a compound or salt in a sterile aqueous or non-aqueous carrier optionally containing a parenterally acceptable oil, for example, polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example, polymeric glycols, gelatins, cocoa-butter or other low melting vegetable waxes or fats or their synthetic analogs.

Typical dermal and transdermal formulations comprise a conventional aqueous or non-aqueous vehicle, for example, a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula (1) or a pharmaceutically acceptable salt thereof calculated as the free acid. Each dosage unit for intranasal administration contains suitably 1-400 mg and preferably 10 to 200 mg per person. A topical formulation contains suitably 0.01 to 5.0% of a compound of Formula (1).

The daily dosage regimen for oral administration is suitably about 0.01 mg/Kg to 40 mg/Kg of a compound of Formula (1) or a pharmaceutically acceptable salt thereof calculated as the free acid. The daily dosage regimen for parenteral administration is suitably about 0.001 mg/Kg to 40 mg/Kg of a compound of Formula (1) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

The biological activity of the compounds of Formula (1) are demonstrated by the following test:

Biological Assay

*S. aureus* or *E. coli* PDF activity is measured at 25° C., using a continuous enzyme-linked assay developed by Lazennec & Meinnel ("Formate dehydrogenase-coupled spectrophotometric assay of peptide deformylase", Anal. Biochem. 1997, 244, pp. 180-182), with minor modifications. The reaction mixture is contained in 50 uL with 50 mM potassium phosphate buffer (pH 7.6), 15 mM NAD, 0.25 U formate dehydrogenase. The substrate peptide, f-Met-Ala-Ser, is included at the KM concentration. The reaction is triggered with the addition of 10 nM Def1 enzyme, and absorbance is monitored for 20 min at 340 nm.

Antimicrobial Activity Assay

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically" (incorporated by reference herein). The compound was tested in serial two-fold dilutions ranging from 0.06 to 64 mcg/ml. A panel of 12 strains were evaluated in the assay. This panel consisted of the following laboratory strains: *Staphylococcus aureus* Oxford, *Staphylococcus aureus* WCUH29, *Enterococcus faecalis* I,

*Enterococcus faecalis* 7, *Haemophilus influenzae* Q1, *Haemophilus influenzae* NEMC1, *Moraxella catarrhalis* 1502, *Streptococcus pneumoniae* 1629, *Streptococcus pneumoniae* N1387, *Streptococcus pneumoniae* N1387, *E. coli* 7623 (AcrABEFD+) and *E. coli* 120 (AcrAB-). The minimum inhibitory concentration (MIC) was determined as the lowest concentration of compound that inhibited visible growth. A mirror reader was used to assist in determining the MIC endpoint.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound according to Formula (1):

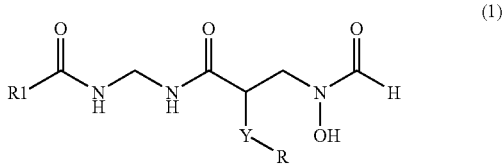

(1)

wherein:

R is selected from the group consisting of:
C$_{2-6}$ alkyl (optionally substituted by alkoxy, halogen, or C$_{1-3}$ alkylsulfanyl); (CH$_2$)$_n$—C$_{3-6}$ carbocycle (optionally substituted by alkoxy, halogen, or C$_{1-3}$ alkylsulfanyl); and (CH$_2$)$_n$—R2, wherein R2 is selected from the group consisting of phenyl, furan, benzofuran, thiophene, benzothiophene, tetrahydrofuran, tetrahydropyran, dioxane, 1,4-benzodioxane or benzo[1,3]dioxole; R2 is optionally substituted by one or more substituent selected from Cl, Br, I, C$_{1-3}$ alkyl (optionally substituted by one to three F) and C$_{1-2}$ alkoxy (optionally substituted by one to three F)};

R1 is selected from the group consisting of aryl and heteroaryl;

Y represents CH$_2$ or a covalent bond; and n is an integer from 0 to 2;

or a pharmaceutically acceptable salt thereof.

2. A compound according to claim 1, with the following absolute configuration:

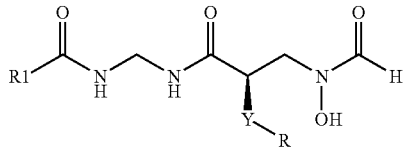

or a pharmaceutically acceptable salt thereof.

3. A compound selected from the group consisting of:
Quinoline-8-carboxylic acid ((R)-2-[(formyl-hydroxy-amino)-methyl]-heptanoylamino}-methyl)-amide;
1,2,3,4-Tetrahydro-quinoline-8-carboxylic acid ({(R)-2-[(formyl-hydroxy-amino)-methyl]-heptanoylamino}-methyl)-amide;
Benzofuran-2-carboxylic acid ({(R)-2-[(formyl-hydroxy-amino)-methyl]-heptanoylamino}-methyl)-amide;
Quinoline-6-carboxylic acid ({(R)-2-[(formyl-hydroxy-amino)-methyl]-heptanoylamino}-methyl)-amide;
1,2,3,4-Tetrahydro-quinoline-6-carboxylic acid ({(R)-2-[(formyl-hydroxy-amino)-methyl]-heptanoylamino}-methyl)-amide;
2,3-Dihydro-benzo[1,4]dioxine-6-carboxylic acid ({(R)-2-[(formyl-hydroxy-amino)-methyl]-heptanoyl]amino}-methyl)-amide;
7-Methoxy-benzofuran-2-carboxylic acid ({(R)-2-[(formyl-hydroxy-amino)-methyl]-heptanoylamino}-methyl)-amide;
5-Methoxy-benzofuran-2-carboxylic acid ({(R)-2-[(formyl-hydroxy-amino)-methyl]-heptanoylamino}-methyl)-amide;
3,4-Dihydro-2H-benzo[b][1,4]dioxepine-7-carboxylic acid ({(R)-2-[(formyl-hydroxy-amino)-methyl]-heptanoylamino}-methyl)-amide;
5-Trifluoromethyl-furan-2-carboxylic acid ({(R)-2-[(formyl-hydroxy-amino)-methyl]-heptanoylamino}-methyl)-amide;
3,4-Difluoro-N-({(R)-2-[(formyl-hydroxy-amino)-methyl]-heptanoylamino}-methyl)-benzamide;
2,3-Difluoro-N-({(R)-2-[(formyl-hydroxy-amino)-methyl]-heptanoylamino}-methyl)-benzamide;
[1,8]Naphthyridine-2-carboxylic acid ({(R)-2-[(formyl-hydroxy-amino)-methyl]-heptanoylamino}-methyl)-amide;
3-Methyl-benzofuran-2-carboxylic acid ({(R)-2-[(formyl-hydroxy-amino)-methyl]-heptanoylamino}-methyl)-amide;
Benzo[1,3]dioxole-5-carboxylic acid ({(R)-2-[(formyl-hydroxy-amino)-methyl]-heptanoylamino}-methyl)-amide;
Benzofuran-2-carboxylic acid {[(R)-2-cyclopentylmethyl-3-(formyl-hydroxy-amino)-propanoylamino]-methyl}-amide; and
Benzofuran-2-carboxylic acid ({(R)-7,7,7-trifluoro-2-[(formyl-hydroxy-amino)-methyl]-heptanoylamino}-methyl)-amide; or a pharmaceutically acceptable salt thereof.

4. A pharmaceutical composition comprising a compound according claim 2 or a pharmaceutically acceptable salt thereof and a pharmaceutically acceptable carrier.

5. A pharmaceutical composition comprising a compound according claim 3 or a pharmaceutically acceptable salt thereof and a pharmaceutically acceptable carrier.

* * * * *